(12) United States Patent
Piraka

(10) Patent No.: US 9,066,715 B2
(45) Date of Patent: Jun. 30, 2015

(54) SURGICAL DEVICE FOR EXCISING CERVICAL OR OTHER TISSUE

(76) Inventor: Hadi A. Piraka, Northville, MI (US)

( * ) Notice: Subject to any disclaimer, the term of this patent is extended or adjusted under 35 U.S.C. 154(b) by 253 days.

(21) Appl. No.: 13/555,575

(22) Filed: Jul. 23, 2012

(65) Prior Publication Data

US 2014/0024966 A1    Jan. 23, 2014

(51) Int. Cl.
*A61B 10/00*    (2006.01)
*A61B 10/02*    (2006.01)

(52) U.S. Cl.
CPC ......... *A61B 10/0233* (2013.01); *A61B 10/0291* (2013.01)

(58) Field of Classification Search
USPC .................. 600/562–567; 606/167, 174, 180
See application file for complete search history.

(56) References Cited

U.S. PATENT DOCUMENTS

| 5,047,042 | A  | 9/1991 | Jerath |
| 5,676,663 | A  | 10/1997 | Kim |
| 6,416,513 | B1 | 7/2002 | Dresden |

*Primary Examiner* — Brian Szmal
(74) *Attorney, Agent, or Firm* — Alex Rhodes

(57) ABSTRACT

A surgical device for excising a tissue sample from a patient. The device includes a pair of articulable plates having blades mounted thereon. A collar is axially moveable along a rotatable actuating member such that the collar induces axial movement of the plates. Cam surfaces cause the plates to move radially inward toward one another, thereby bringing the blades toward one another so as to cut the tissue sample from the patient.

11 Claims, 4 Drawing Sheets

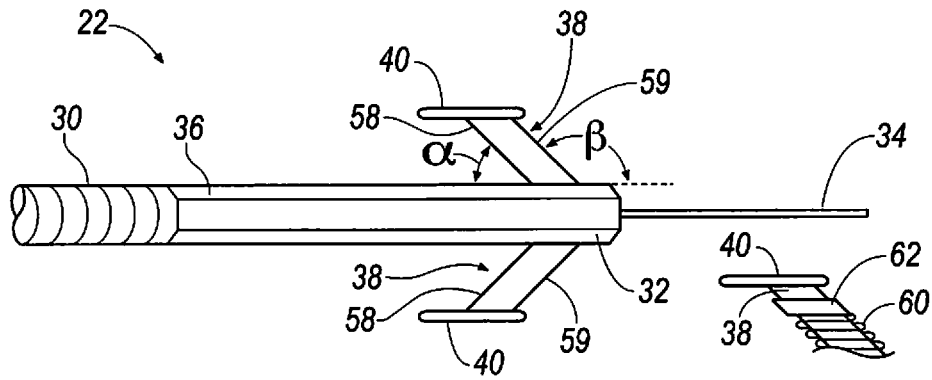
FIG. 4A
FIG. 4B
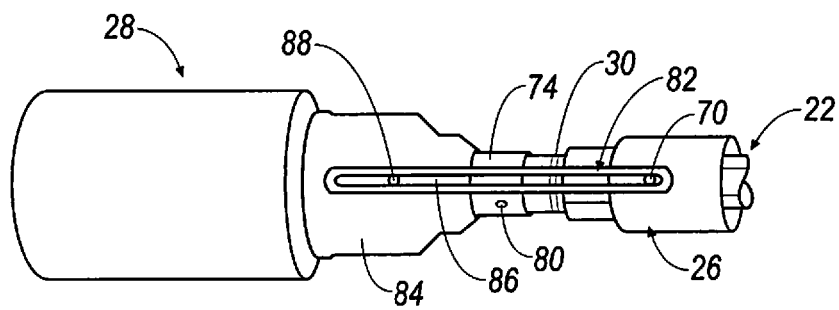
FIG. 5
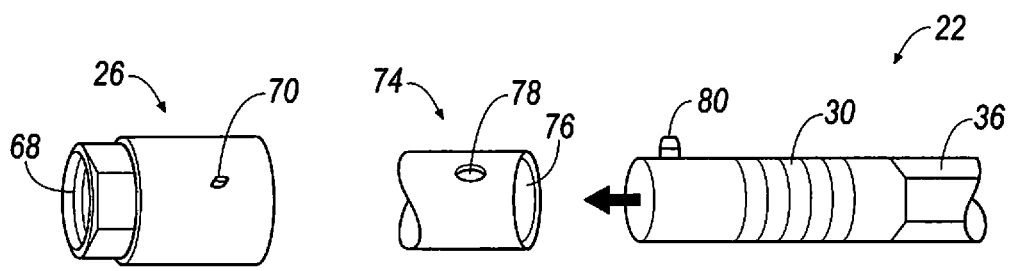
FIG. 6
FIG. 7

SURGICAL DEVICE FOR EXCISING CERVICAL OR OTHER TISSUE

BACKGROUND

1. Field of the Invention

The present invention generally relates to surgical devices, and more particularly relates to devices used to excise a tissue sample from a patient.

2. Related Technology

For the diagnosis of cancer, or pre-cancerous tissue, it is often necessary to excise a tissue sample from a patient. One particular type of cancer where obtaining a sample is problematic is cervical cancer. Typically, a cone-shaped sample is removed for pathological analysis. During this procedure, generally called conization, a cone-shaped section of the uterine cervix is formed. This is often achieved by either cutting the cervix with a knife (termed the "cold knife" procedure) or cautery (burning) by a LEEP (loop electrosurgical excision procedure) or laser beam.

Each one of these two methods is time consuming and produces an irregular cervical tissue sample. There are also other drawbacks with these techniques. With the LEEP or laser procedure, the margins of the cone shaped tissue sample may be subjected to burning. This burning may mask the true nature of the tissue and render the pathological diagnosis difficult.

Accordingly, what is needed is a device that produces a tissue sample with regular margins and which does not cause burning of the edges of the tissue sample.

SUMMARY

In meeting the challenges outlined above and overcoming the limitations of the known technology, the present invention provides for a surgical device that may be used to excise cervical or other tissue. With the present invention, once the device is positioned relative to the location where the sample is to be obtained, a set of blades are rotated and advanced into the tissue. As the blades are advanced, the blades are drawn inward toward one another until the tissue is excised. As a result of the advancing and closing blades, a tissue sample is formed in a generally conical shape, with clean and consistent marginal sides. Additionally, the tissue sample is retained in the compartment formed by the closed blades until removed from the vicinity of the patient. The tissue sample may then be released into a proper specimen container.

In one aspect, the present invention relates to surgical devices for excising a tissue sample, the device comprising a rod located in a sleeve, wherein the sleeve has portions defining articulating plates, the ends of which include cutting blades. The rod includes two angled arms that define cam surfaces extending at an acute angle from the rod. The arms extend through slots formed in the sleeve. A collar is provided on a threaded end of the rod and is engaged with the rod such that the collar can rotate relative to the rod. An actuator causes rotation of the rod, and relative rotation between the collar and the rod. Resulting from the relative rotation between the rod and the collar, axial motion is imparted to the collar, and this axial motion causes the cam surfaces to interact with the sleeve, thereby cause the articulating plates to move axially and to deflect inwardly toward one another. With inward and axial movement of the distal ends of the articulating plates, the cutting blades are able to excise a tissue sample that is generally conical in shape with a well-defined perimeter.

In another aspect of the invention, the present invention provided in an embodiment wherein a rod is provided with an inner sleeve and both the inner sleeve and the rod are received within an outer sleeve. The inner sleeve has two articulating plates, each of which includes a protrusion defining cam surfaces and a cutting blade on its distal end. The protrusions are positioned so as to initially extend through openings provided in the outer sleeve. A collar is provided on a threaded end of the rod and is engaged with the rod such that the collar can rotate relative to the rod. When an actuator causes rotation of the rod, the collar does not rotate. Resulting from the relative rotation between the rod and the collar, axial motion is imparted to the collar, and this axial motion causes the outer sleeve to axially move relative to the inner sleeve. As the outer sleeve advances over the inner sleeve, the ends of the openings in the outer sleeve ride over cam surfaces on the protrusions. As a result, the protrusions and the articulating plates are forced to deflect inwardly and toward one another. With inward and axial movement of the of the distal ends of the articulating plates and the cutting blades, the cutting blades are able to excise a tissue sample that is generally conical in shape with a well-defined perimeter Further objects, features and advantages of this invention will become readily apparent to persons skilled in the art after a review of the following description, with reference to the drawings and claims that are appended to and form a part of this specification.

BRIEF DESCRIPTION OF THE DRAWINGS

FIG. 4A shows the interior components, the rod, arms and probe, of the device seen in FIG. 1-3.

FIG. 4B shows an alternative configuration for the ends of the arms seen in FIG. 4A.

FIG. 5 is a side view of an actuator mechanism assembled with the rod and collar of the device seen in FIG. 1.

FIG. 6 is a side view of a collar (nut), as used in the device of FIG. 5.

FIG. 7 is a side view of a portion of a connection between the actuator and the rod of the device of FIG. 1.

DETAILED DESCRIPTION

Figure 1:
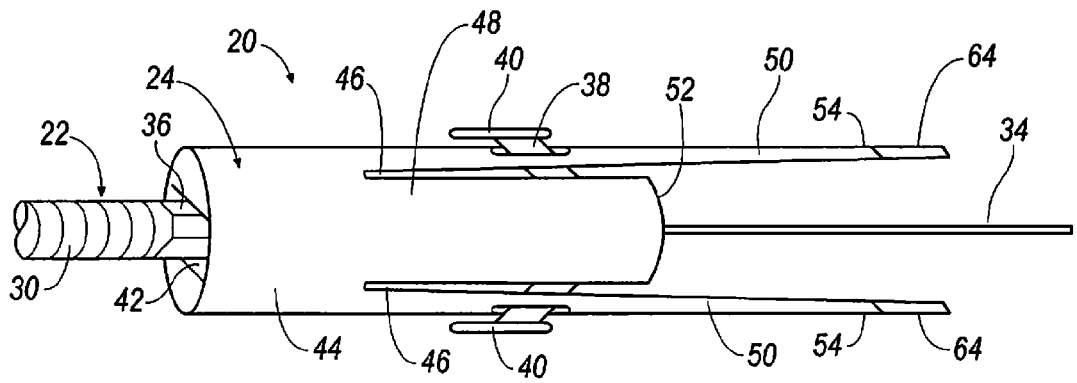
FIG. 1 is an external side view of a device embodying the principles of the device shown in FIG. 1.
Figure 2:
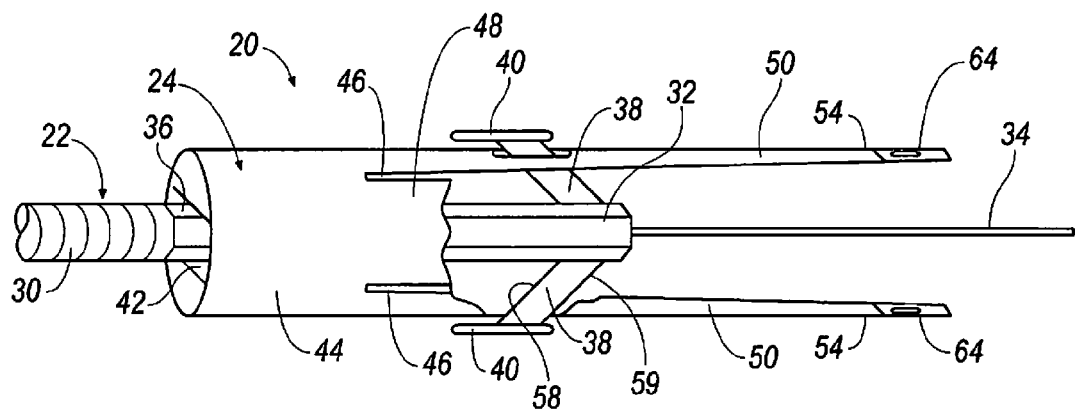
FIG. 2 is a side view of the device seen in FIG. 1, with portions broken away to show internal components thereof.

The present invention is a surgical device that, when actuated, has the ends of two substantially triangular plates move towards each other. Provided at the ends of the plates are blades and, as such, the device may be used to cut tissue. For example, the device may be used to excise tissue from a cervix for further pathological analysis.

Referring now to the drawings, a first embodiment of a surgical device (20) according to the principles of the present invention is depicted in FIGS. 1-8. The device (20) includes, as it primary components, an actuation rod (22), a cylindrical sleeve (24), a collar (26) and a drive mechanism or actuator (28).

The actuation rod (22) has opposing ends, one of which is threaded and herein referred to as the threaded end (30). The opposing end (32) has a slender probe (34) extending therefrom; the probe (34) has a diameter that is substantially smaller than the rod (22) itself. Adjacent to the threaded end (30), the rod (22) is formed with a keyed surface (36). The keyed surface (36) may have any desired shape and, in the figures, the keyed surface (36) is illustrated in its simplest form, a flat surface. As will be more apparent from the discussion that follows, the shape of the keyed surface (36) must be such that it allows the rod (22) to rotate with and axially slide relative to another component, the sleeve (24).

Extending generally from the opposing end (32) of the rod (22) is a pair of arms (38). In this first embodiment, the arms (38) are angled relative to the rod (22) in a direction away from the probe (34) and toward the threaded end (30). The outwardly terminal ends of the arms (38) are provided with an enlargement or stop (40).

The rod (22) is received in and extends through the sleeve (24). Where the rod (22) enters into the sleeve (24), the end of the sleeve (24) is formed with a keyed slot (42) whose shape is complementary to that of the keyed surface (36). In the illustrated embodiment, the key slot (42) is shown as a slot extending the full width of the sleeve (24). However, it will be appreciated that the keyed slot (42) may have a shape that is complementary with circumferential shape of the rod (22) in the area of the keyed surface (24). As noted above, the engagement and interaction of the keyed surface (36) and the keyed slot (42) allow for the sleeve (24) to rotate with the rod (22) while allowing for the sleeve (24) to move axially along the rod (22).

The sidewall (44) of the sleeve (24) defines a hollow interior cavity within which the rod (22) is received. The sidewall (44) is further provided with two sets of cuts (46), extending longitudinally along the sleeve (24) from the end of the sleeve (24) opposite of the keyed slot (42). The two sets of cuts (46) divide the sleeve (24) into two pairs of wall plates (48, 50), wherein each pair is comprised of diametrically opposed individual plates and are herein referred to as side plates (48) and articulating plates (50). The articulating plates (50) extend beyond the terminal ends (52) of the side plates (48) and are generally triangularly shaped so converge toward a point at their own distal ends (54). As their name implies, the articulating plates (50) are intended to be moveable and for this reason the sleeve (22) if formed at a thickness and of a material (plastic or metal) that allows for bending of the articulating plates (50) toward one another.

To facilitate the bending of the articulating plates (50) toward one another, the articulating plates (50) are further provided with slots (56), through which the angled arms (38) of the rod (22) extend. The stops (40) on the ends of the arms (38) are therefore located exteriorly of the sleeve (24) and may be larger in width than the slots and shaped to conform to the exterior surface of the sleeve (24).

Being angled, the arms (38) define cam surfaces (58, 59), which are the surfaces of the arms (38) that define an acute angle α and an obtuse angle β with respect to the rod (22). When the sleeve (24) is axially advanced along and with respect to the rod (22), the cam surfaces (58) engage the ends of the slots (56). Further movement of the sleeve (24) relative to the rod (22), to the right in the figures, causes the ends of the slots (56) to ride downward along the closing cam surfaces (58) toward the rod (22). This action causes the articulating plates (50) to bend toward one another, as seen in FIG. 3.

Axial movement in the opposite direction, toward the left in the figures, causes the opposing end of the slot (56) to ride upward along opening cam surfaces (59), thereby separating the distal ends (54) of the articulating plates (50) from one another. Optionally, a spring (60) and ring (62) may be provided on the arms (38), as illustrated in FIG. 4B. The spring (60) and ring (62) are located interiorly of the articulating plate (50) and assist in returning the articulating plates (50) to their outward or open positions.

The articulating plates (50), at their distal ends (54), are integrally formed with cutting blades (64). The blades (64) may be unitarily formed as the ends (54) of the plates (50) or, alternatively, may be detachably engaged with the ends (54) of the plates (50) in a known manner.

Figure 3:
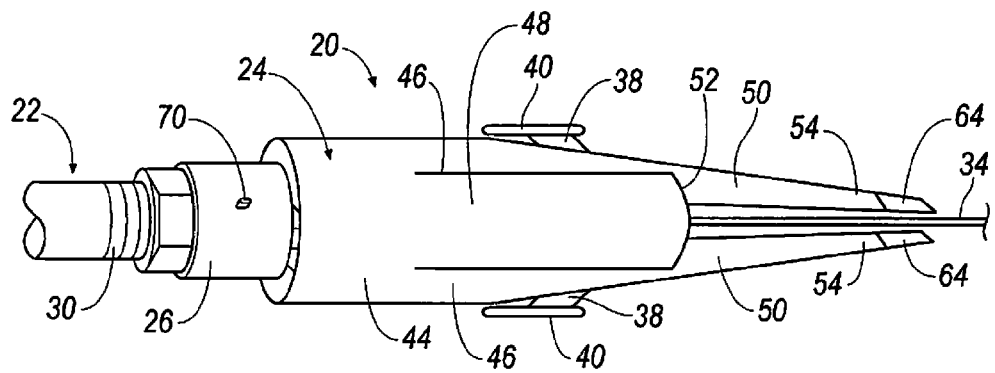
FIG. 3 is a side view of the device of FIG. 1 with the cylinder advanced and the blades brought towards each other.

As seen in FIGS. 3 and 5, provided on the threaded end (30) of the rod (22) is a collar or nut (66). The collar (26) is internally threaded (68) and includes a pin (70) protruding from an exterior surface (72) of the collar (26). The internal threads (68) allow the collar (26) to engage the threaded end (30) of the rod (22) and, as further discussed below, the pin (70) is used to prevent rotation of the collar (26). Engaged in this manner, by rotating the rod (22) relative to the collar (26), the collar (26) is caused to axially move along the length of the threaded end (30). The direction of movement will accordingly depend on the direction of rotation of the rod (22). The collar (26) is shown individually in FIG. 6.

The actuator (28) is a rotary actuator and is used to drive or impart rotation to the rod (22). It includes a motor (not shown) for rotating an output member or driver (74) and may be either battery, pneumatically or electrically driven. To connect the actuator (28) to the rod (22), the driver (74) of the actuator (28) is engaged with the end (30) of the rod (22), but not the threads on this end (30). To create this engagement, the driver (74) is provided with an inner bore (76) into which the end (30) is received. The driver (74) further includes an aperture (78) extending through the sidewall of the driver (74). When the end (30) of the rod (22) is inserted into the bore (76), a spring loaded detent pin (80) provided on the end (30) of the rod (22) is brought into engagement with the aperture (78), thereby interlocking the driver (74) with rod (22) such that rotation of the driver (74) will impart rotation to the rod (22).

The actuator (28) is also connected to the collar (26). This connection, however, is configured to prevent rotation of the collar (26). To prevent rotation of the collar (26), a rail (82) extends between the collar (26) and the housing (84) of the actuator (28), generally with one end of the rail (82) attached to the housing (84) and the other end of the rail (82) attached to the collar (26). The rail (82) is further provided with a slot (86) and the pin (70) located on the collar (26) is slideably retained within the slot (86). Where engaged with the actuator (28), the rail (82) is similarly engaged with a pin (88) provided on the housing (84). Alternatively, the rail (82) may be engaged with one of the housing (84) or the collar (26), but not both, such that the engagement is a fixed engagement. Engaged in the manner, the rail prevents rotation of the collar (26).

Upon rotation of the rod (22), the rail (82) will prevent rotation of the collar (26) and the threaded engagement of the collar (26) with the rod (22) will cause the collar (26) to move axially along the rod (22).

Beginning with the device (20) in the position of FIG. 1, the probe (34) is inserted into the tissue where the sample is to be removed. The probe (34) therefore guides the device (20) to remove the sample from the precise area under examination. When the rod (22) is rotated, the collar (26) moves axially along the rod (22) toward the right in FIG. 1, the collar (26) will abut against the end of the sleeve (24). Since the sleeve

(24) is also axially moveable relative to the rod (22), the sleeve (24) will be caused to axially move relative to the rod (22). This in turn will cause the ends of the slots (56) to engage the closing cam surfaces (58), forcing the blades (64) on the distal ends (54) of the articulating plates (50) toward each other. Since the sleeve (24) rotates with the rod (22), the blades (64) are rotated at the same rate as the rod (22) as they are brought together. This action, deflection of the articulation plates (50) towards each other while being rotated, will cause a cut in a tissue, such as a cervix, when the blades engage the tissue.

At some point, the collar (26) may have traveled along the entire length of the threads (30) along the rod (22). At this point, the collar (26) stops advancing the sleeve (24) relative to the rod (22), thereby limiting advancement of the blades (64) into the tissue.

The device (20) will now be generally described in connection with a conization procedure of the cervix.

To employ the device, an initial evaluation of the size and shape of the subject's cervix and the required diameter of the desired cone (e.g., 1 cm, 2 cm, or 3 cm) is carried out. The cervix is thereafter dilated with common dilators used in the art. After grasping the cervix with a tennaculum, the probe (34) is inserted in the endocervix. After the blades (64) have been brought in close proximity with the surface of the cervix, the actuator (28) is activated and held in place (i.e., not moved) until the process of conization is complete. Upon activation of the actuator (28), the blades (64) will be automatically advanced a desired length (e.g., about 2-3 cm) and, as a result of the articulating plates (50) being deflected towards each other, the rotation of the blades (64) will result in a cut into the tissue, a barrel shape at first and then cone shaped, to a typical total depth off about 20 to 30 mm. The width between the blades (64) before conization is preferably in the range of 10 to 30 mm. The total width between the ends of the blades (64) after conization is preferably 0 to 3 mm.

After completing the cutting of the tissue sample, the device (20) is then pulled out and the actuator (28) is reversed, opening and separating the blades (64) from each other. The cone shaped tissue sample is then removed from the probe (34) and pathologically evaluated for evidence of precancerous or cancerous tissue.

Figure 9:
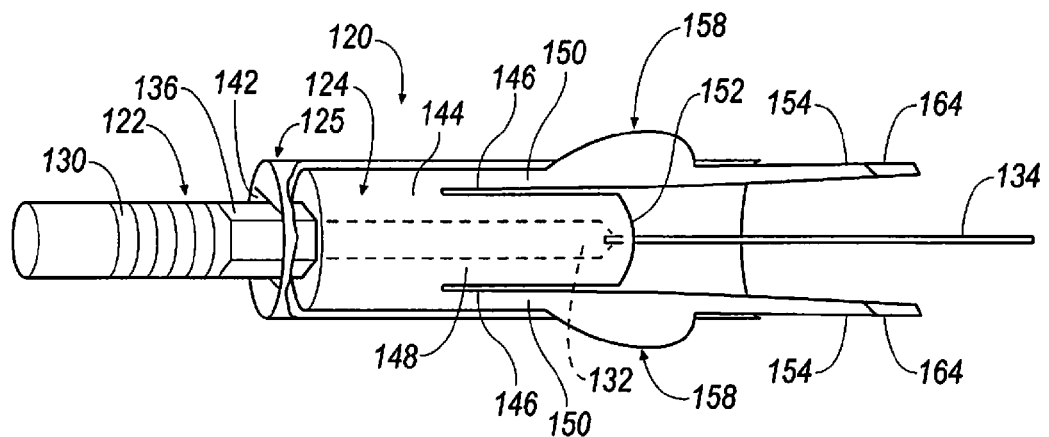
FIG. 9 is a view similar to FIG. 8 with portions broken away to show inner cylinder and first rod of the device.
Figure 8:
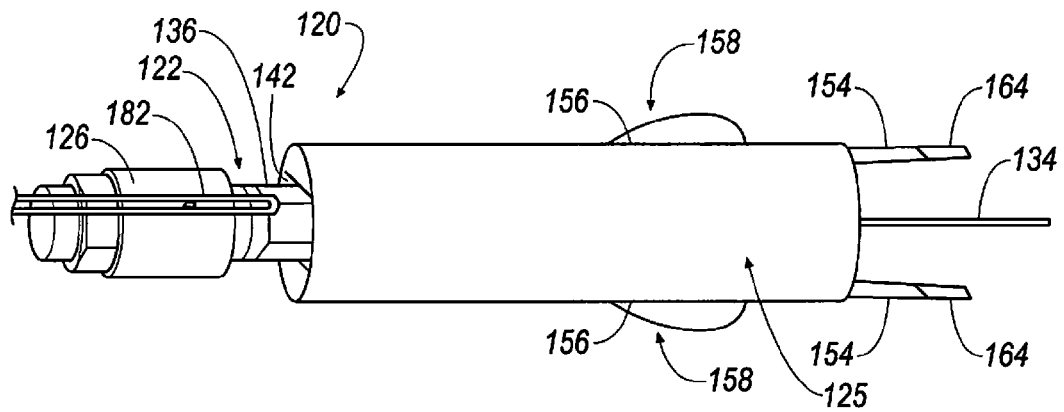
FIG. 8 is a side view of an alternative embodiment of the present invention.
Figure 10:
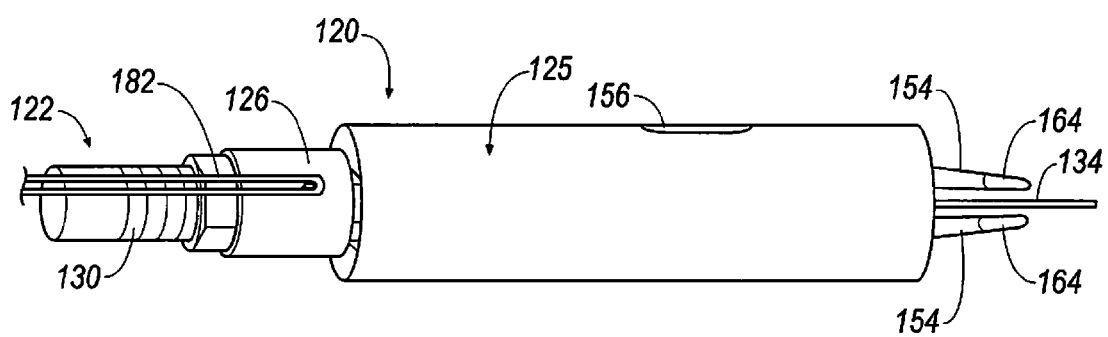
FIG. 10 is a side view of the device of FIG. 8 with the inner cylinder advanced and the blades brought together and towards each other.
Figure 11:
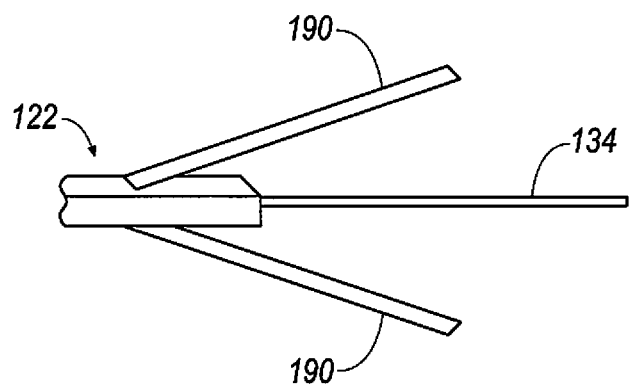
FIG. 11 is view of a portion of the first rod with two optional springs attached to the first rod of the device seen in FIG. 8.

A second embodiment of the invention is depicted in FIGS. 8-10.

The device (120) includes, as it primary components, an actuation rod (122), a cylindrical inner sleeve (124), an outer sleeve (125), a collar (126) and an actuator (not shown).

The actuation rod (122) has opposing ends, one of which is threaded (the threaded end (130)) and the opposite of which (the opposing end (132)) has a slender probe (134) extending therefrom. Adjacent to the threaded end (130), the rod (122) is formed with a keyed surface (136). The keyed surface (136) may have any desired shape and is simply illustrated as a flat surface.

Provided on the rod (122) and fixed relative thereto is the inner sleeve (124). The inner sleeve (124) includes a sidewall (144) that defines a hollow interior cavity within which a portion of the rod (122) extends. The sidewall (144) has two sets of cuts (146), extending longitudinally along the sleeve (124) from the one end thereof. The two sets of cuts (146) divide the sleeve (124) into two pairs of wall plates (148, 150), wherein each pair is comprised of diametrically opposed individual plates and are herein referred to as side plates (148) and articulating plates (150). The articulating plates (150) extend beyond the terminal ends (152) of the side plates (148) and are generally shaped so converge toward a point at their own distal ends (154). The articulating plates (150) are deflectable and therefore the sleeve (122) if formed at a thickness and of a material (plastic or metal) that allows for deflection or bending of the plates (150) toward one The inner sleeve (124) is received in the outer sleeve (125) and the rod (122) extends from the outer sleeve (125) through a keyed slot (142), whose shape is complementary to that of the keyed surface (136) on the rod. As with the prior embodiment, the keyed slot (142) may have a shape that is complementary with circumferential shape of the rod (122) in the area of the keyed surface (136). As previously noted, engagement and interaction of the keyed surface (136) and the keyed slot (142) allow for the outer sleeve (125) to rotate with the rod (122) while allowing the outer sleeve (125) to move axially along the rod (122).

To facilitate the deflection of the articulating plates (150) toward one another, the articulating plates (150) include protrusions (158) that define cam surfaces. The protrusions (158) extend outwardly through openings (156) formed in the outer sleeve (125). The cam surfaces of the protrusions (158) are surfaces that are angled relative to the rod (122). When the outer sleeve (125) is axially advanced along and with respect to the inner sleeve (124) and the rod (122), the cam surfaces of the protrusions (158) engage the ends of the openings (156). Further movement of the outer sleeve (125) relative to the inner sleeve (124) causes the ends of the openings (156) to ride onto the cam surfaces of the protrusions (158), thereby deflecting the articulating plates (150) inwardly and toward one another, as seen in FIG. 10. Axial movement in the opposite direction, toward the left in FIGS. 8-10, allows the articulating plates (150) to resume their pre-deflected position, either by virtue of the inherent resiliency of the material forming the articulating plates (150) or a biasing member/spring (190) provided with the rod (122).

The articulating plates (150), at their distal ends (154), are integrally formed with cutting blades (164). The cutting blades may be unitarily formed as the ends (54) of the plates (50) or detachably engaged with the ends (154) of the plates (150) in a known manner.

As seen in FIGS. 8 and 10, provided on the threaded end (130) of the rod (122) is a collar or nut (126). The collar (126), its mounting to the rod (122), the actuator, and the actuator's engagement/operation with the collar (128) and the rod (122), is identical to that in the prior embodiment. In that regard, reference is hereby made to the discussion in connection with the prior embodiment.

Accordingly, upon rotation of the rod (122) by the actuator, a rail (182) will prevent rotation of the collar (126) and the threaded engagement between the collar (126) and the rod (122) will cause the collar (126) to move axially along the rod (122). When the rod (122) is rotated, the collar (126) moves axially along the rod (122) toward the right in FIGS. 8-10. The collar (126) will abut against the end of the outer sleeve (125). Since the outer sleeve (125) is also axially moveable relative to the rod (122), the outer sleeve (125) will axially move relative to the rod (122). This in turn will cause the ends of the slots (156) to engage the closing cam surfaces of the protrusions (158), forcing the blades (164) toward each other. Since the both the outer and inner sleeves (124, 125) rotate with the rod (122), the blades (164) are rotated at the same rate as the rod (122) as they are brought together. This action, deflection of the articulation plates (150) towards each other, while being rotated, will cause a cut in a tissue, when the blades engage the tissue.

Optionally, the rod (122) may include two or more springs (190), which protrude towards the probe (134) and laterally away from the rod (122). The springs (190) operate to bias the articulating plates (150) outwardly so that the plates (150)

return to their outward position, with the protrusions (150) extending through the openings (156), upon movement of the outer sleeve (125) back to its initial position, as seen in FIGS. 8 and 9.

As a person skilled in the art will readily appreciate, the above description is meant as an illustration of implementation of the principles this invention. This description is not intended to limit the scope or application of this invention in that the invention is susceptible to modification, variation and change, without departing from spirit of this invention, as defined in the following claims.

What is claimed:

1. A surgical device for excising a tissue sample, the device comprising: an actuating member having a first and second ends; a cylindrical sleeve defining a hollow interior, said actuating member being provided at least partially within the hollow interior, said sleeve having portions defining at least two articulable plates having cutting blades provided on distal ends thereof, said plates being resiliently moveable such that said cutting ends of said blades are moveable inwardly toward one another when said actuating member is rotated, an actuator coupled to said actuating member, said actuator configured to cause rotation of said actuating member; and a collar threadably attached to an end portion of said sleeve opposite said cutting end portions of said blades for causing axial movement of said sleeve during rotational movement of said actuating member whereby said cutting end portions of said blades are moved inwardly toward one another so as to remove a tissue sample from surrounding tissue.

2. A surgical device for excising a tissue sample comprising: an actuating member having a threaded section, said actuating member further having a keyed surface provided adjacent to said threaded section; a cylindrical sleeve defining a hollow interior, said sleeve having portions defining at least two articulable plates having cutting blades mounted on distal ends thereof, said plates being resiliently moveable inwardly toward one another, said sleeve further including a keyed opening through which said keyed surface of said actuating member is extended, said keyed opening corresponding in shape to said keyed surface such that said sleeve is axially moveable along said actuating member and rotatable with said actuating member; an actuator coupled to said actuating member, said actuator connected to said actuating member to cause rotation of said actuating member; a collar threadably engaged with said threaded section of said actuating member and being fixed for relative rotation with respect to said actuating member, whereby relative rotation of the collar with respect to the actuating member causes said collar to axially move along said actuating member, said collar coupled to said sleeve such that axial movement of said collar induces axial movement of said sleeve; at least one arm extending outwardly from said actuating member, said arm having a cam surface, said cam surface configured to engage a portion of said sleeve during axial movement of said sleeve along said actuating member; and said actuator is configured to cause rotation of said actuating member and relative axial motion of said collar and said sleeve relative to said actuating member, said axial motion of said sleeve causes said cam surfaces to engage with a portion of said sleeve thereby causing said articulable plates to deflect toward one another moving said blades inwardly toward one another so as to remove said tissue sample from surrounding tissue.

3. The device of claim 2, wherein said collar is internally threaded.

4. The device of claim 2, wherein said threaded section of said actuating member is located toward a first end thereof.

5. The device of claim 2, further comprising a rail extending between said actuator and said collar.

6. The device of claim 5, wherein said rail slideably engages said actuator or said collar.

7. The device of claim 5, wherein said rail is configured to inhibit rotation of said collar with rotation of said actuating member.

8. The device of claim 2, wherein said actuating member is rod shaped and includes a second end opposite of said threaded section, said second end having a probe extending therefrom, said probe having a smaller diameter than said first end of said actuating member.

9. The device of claim 2, wherein each of said articulable plates has an opening formed therein and one of said arms of said actuating member extends through each of said-openings.

10. The device of claim 9, wherein said-portions of said articulating plates engaged by said cam surfaces of said arms are said portions defining said openings in said articulating plates.

11. The device of claim 2, wherein said blades define a retaining cavity for said tissue sample when said blades are brought towards one another.

* * * * *